United States Patent
Hu et al.

(10) Patent No.: US 11,564,612 B2
(45) Date of Patent: Jan. 31, 2023

(54) AUTOMATIC RECOGNITION AND CLASSIFICATION METHOD FOR ELECTROCARDIOGRAM HEARTBEAT BASED ON ARTIFICIAL INTELLIGENCE

(71) Applicant: Shanghai Lepu CloudMed Co., Ltd, Shanghai (CN)

(72) Inventors: Chuanyan Hu, Beijing (CN); Xue Zhang, Beijing (CN); Liang Tian, Beijing (CN); Tao Liu, Beijing (CN); Jun Cao, Beijing (CN); Chang Liu, Beijing (CN)

(73) Assignee: Shanghai Lepu CloudMed Co., Ltd, Shanghai (CN)

( * ) Notice: Subject to any disclaimer, the term of this patent is extended or adjusted under 35 U.S.C. 154(b) by 380 days.

(21) Appl. No.: 16/755,105

(22) PCT Filed: Jan. 12, 2018

(86) PCT No.: PCT/CN2018/072350
§ 371 (c)(1),
(2) Date: Apr. 9, 2020

(87) PCT Pub. No.: WO2019/100562
PCT Pub. Date: May 31, 2019

(65) Prior Publication Data
US 2020/0237246 A1  Jul. 30, 2020

(30) Foreign Application Priority Data
Nov. 27, 2017 (CN) .......................... 201711203546.7

(51) Int. Cl.
*A61B 5/349* (2021.01)
*G16H 40/63* (2018.01)
(Continued)

(52) U.S. Cl.
CPC .......... *A61B 5/349* (2021.01); *G06K 9/00536* (2013.01); *G06N 3/08* (2013.01);
(Continued)

(58) Field of Classification Search
CPC ................................ A61B 5/349; G16H 40/63
(Continued)

(56) References Cited

U.S. PATENT DOCUMENTS

| 7,996,075 | B2 | 8/2011 | Korzinov et al. |
| 9,408,543 | B1 | 8/2016 | Gupta et al. |

(Continued)

FOREIGN PATENT DOCUMENTS

| CN | 102697492 B | 8/2014 |
| CN | 104161510 | 3/2016 |

(Continued)

OTHER PUBLICATIONS

Chinese First Office Action for Chinese Application No. 201711203546.7 dated Apr. 2, 2020, 9 pages.
(Continued)

*Primary Examiner* — Nadia A Mahmood
(74) *Attorney, Agent, or Firm* — TraskBritt (57) ABSTRACT

An automatic recognition and classification method for electrocardiogram heartbeat based on artificial intelligence, comprising: processing a received original electrocardiogram digital signal to obtain heartbeat time sequence data and lead heartbeat data; cutting the lead heartbeat data according to the heartbeat time sequence data to generate lead heartbeat analysis data; performing data combination on the lead heartbeat analysis data to obtain a one-dimensional heartbeat analysis array; performing data dimension amplification and conversion according to the one-dimensional heartbeat analysis array to obtain four-dimensional tensor data; and inputting the four-dimensional tensor data
(Continued)

to a trained LepuEcgCatNet heartbeat classification model, to obtain heartbeat classification information. The method overcomes the defect that the conventional method only depends on single lead independent analysis for result summary statistics and thus classification errors are more easily obtained, and the accuracy of the electrocardiogram heartbeat classification is greatly improved.

16 Claims, 5 Drawing Sheets

(51) Int. Cl.
*G06K 9/00* (2022.01)
*G06N 3/08* (2006.01)
*A61B 5/0245* (2006.01)
*A61B 5/00* (2006.01)

(52) U.S. Cl.
CPC ............ *G16H 40/63* (2018.01); *A61B 5/0245* (2013.01); *A61B 5/7267* (2013.01)

(58) Field of Classification Search
USPC ........................................................ 600/519
See application file for complete search history.

(56) References Cited

U.S. PATENT DOCUMENTS

| | | | |
|---|---|---|---|
| 2004/0059237 | A1 | 3/2004 | Mathur et al. |
| 2007/0167846 | A1 | 7/2007 | Sternickel et al. |
| 2007/0260151 | A1 | 11/2007 | Clifford |
| 2013/0117207 | A1 | 5/2013 | Kim et al. |
| 2016/0120433 | A1 | 5/2016 | Hughes et al. |

FOREIGN PATENT DOCUMENTS

| | | |
|---|---|---|
| CN | 106725420 A | 5/2017 |
| CN | 107203692 A | 9/2017 |
| CN | 105092266 | 10/2017 |
| CN | 107358196 A | 11/2017 |
| CN | 107137072 B | 9/2019 |
| CN | 106108889 B | 11/2019 |
| CN | 106214145 B | 12/2019 |
| JP | 2017-524104 A | 8/2017 |
| WO | 2015/051280 A1 | 4/2015 |
| WO | 2017/091736 A1 | 6/2017 |

OTHER PUBLICATIONS

Indian Office Action for Indian Application No. 202047017125 dated May 30, 2021, 5 pages.
Acharya et al., A Deep Convolution Neural Network Model to Classify Heartbeats, Computers in Biology and Medicine, (Aug. 2017), 19 pages.
Chinese Office Action for Chinese Application No. 201711203546.7 dated Feb. 4, 2020, 7 pages.
Chinese Search Report for Chinese Application No. 201711203546.7 dated Feb. 4, 2020, 2 pages.
International Search Report for International Application No. PCT/CN2018/072350 dated Aug. 27, 2018, 2 pages.
International Written Opinion for International Application No. PCT/CN2018/072350 dated Aug. 27, 2018, 3 pages.
Isin et al., Cardiac Arrhythmia Detection Using Deep Learning, Procedia Computer Science, vol. 120, (2017), pp. 268-275.
Kossaifi et al., Tensor Contraction Layers for Parsimonious Deep Nets, 2017 IEEE Conference on Computer Vision and Pattern Recognition Workshops, (2017), pp. 1940-1946.
Yu et al., Research on Soft and Hard Tactile Sensing Method Based on Convolutional Neural Network, Transducer and Microsystem Technologies, (2017), pp. 35-41.
European Search Report and Search Opinion Received for EP Application No. 18880577, dated on Jun. 9, 2021, 8 pages.
Japanese Office Action and Search Report for Japanese Application No. 2020-518512 dated May 11, 2021 with machine translation, 6 pages.
Tahsin Reasat et al.: "Detection of Inferior Myocardial Infarction using Shallow Convolutional Neural Networks", arxiv.org, Cornell University Library, 201 Olin Library Cornell University Ithaca, NY 14853, Oct. 3, 2017 (Oct. 3, 2017).
Japanese Applicataion for Japanese Application No. 2020-591166 dated Dec. 8, 2020, 10 pages with machine translation.

AUTOMATIC RECOGNITION AND CLASSIFICATION METHOD FOR ELECTROCARDIOGRAM HEARTBEAT BASED ON ARTIFICIAL INTELLIGENCE

CROSS-REFERENCE TO RELATED APPLICATIONS

This application is a national phase entry under 35 U.S.C. § 371 of International Patent Application PCT/CN2018/072350, filed Jan. 12, 2018, designating the United States of America and published as International Patent Publication WO 2019/100562 A1 on May 31, 2019, which claims the benefit under Article 8 of the Patent Cooperation Treaty to Chinese Patent Application Serial No. 201711203546.7, filed Nov. 27, 2017.

TECHNICAL FIELD

The present disclosure relates to the technical field of artificial intelligence-assisted data analysis and processing, and more particularly, to an automatic identification and classification method of electrocardiogram heart beat based on artificial intelligence.

BACKGROUND

A Cardiovascular disease is one of main diseases that threaten human health. A detection of the cardiovascular disease with effective means is currently an important topic that attracts a worldwide attention. Electrocardiogram (ECG) is a main method for diagnosing the cardiovascular disease in modern medicine. Using the ECG to diagnose various cardiovascular diseases is essentially a process of extracting characteristic data of the ECG to classify the ECG. During the process for reading and analyzing the ECG, experts and doctors need to compare previous changes of signals of each lead (except for single-lead data) on the time sequence, and a correlation (spatial relationship) and variation between leads at the same time, and then an accurate judgment can be made. However, the accuracy cannot be guaranteed in the way that depends on experiences of the doctors.

With the development of science and technology, an automatic and accurate analysis of the ECG by using a computer has been rapidly developed. However, although most ECG analysis software in the market can automatically analyze the data, due to a complexity and variability of ECG signals themselves, the accuracy of the current automatic analysis software is far from enough to meet requirements of clinical analyses.

BRIEF SUMMARY

The purpose of the present disclosure is to provide an automatic identification and classification method of ECG heart beat based on artificial intelligence, which overcomes a defect that traditional methods, which only rely on independent analyses of a single lead for summarizing result and doing statistics would easily cause classification errors, and greatly enhances an accuracy of the heart beat classification.

To achieve the above purpose, the present disclosure provides an automatic identification and classification method of ECG heart beat based on artificial intelligence, including:

processing received original ECG digital signals to generate heart beat time sequence data and lead heart beat data;

cutting the lead heart beat data with a set data amount to generate lead heart beat analysis data, according to the heart beat time sequence data;

performing data combination on the lead heart beat analysis data to obtain a one-dimensional heart beat analysis array;

performing data dimension amplification conversion on the one-dimensional heart beat analysis array to obtain four-dimensional tensor data; and inputting the four-dimensional tensor data into a trained LepuEcgCatNet heart beat classification model to obtain heart beat classification information corresponding to the lead heart beat analysis data.

Preferably, the cutting the lead heart beat data with a set data amount to generate lead heart beat analysis data according to the heart beat time sequence data, includes:

determining a center sample point of the lead heart beat data according to the heart beat time sequence data; and taking the center sample point as a center, according to time characterization data and a preset data sample frequency, sampling the lead heart beat data to both sides with the set data amount, so as to obtain the lead heart beat analysis data.

Preferably, the lead heart beat analysis data is single-lead heart beat analysis data, and the performing data combination on the lead heart beat analysis data to obtain a one-dimensional heart beat analysis array includes:

combining the single-lead heart beat analysis data into the one-dimensional heart beat analysis array according to the heart beat time sequence data.

Preferably, the lead heart beat analysis data is multi-lead heart beat analysis data, and the performing data combination on the lead heart beat analysis data to obtain a one-dimensional heart beat analysis array includes:

combining the multi-lead heart beat analysis data into the one-dimensional heart beat analysis array according to lead parameters and the heart beat time sequence data.

Preferably, the performing data dimension amplification conversion on the one-dimensional heart beat analysis array to obtain four-dimensional tensor data includes:

converting the one-dimensional heart beat analysis array into a four-dimensional tensor data input format required by the trained heart beat classification model in a specific conversion mode; wherein the four-dimensional tensor data has four factors, which are height data, width data, channel data and batch data.

Wherein the specific conversion mode includes:

determining the height data and the width data according to a length of input samples, and generating fusion data according to the height data, the width data or the channel data; wherein the channel data is a number of leads; and generating the four-dimensional tensor data according to the batch data and the fusion data; wherein the batch data is a number of the input samples.

Preferably, the inputting the four-dimensional tensor data into a trained LepuEcgCatNet heart beat classification model to obtain heart beat classification information corresponding to the lead heart beat analysis data includes:

according to the LepuEcgCatNet heart beat classification model, performing layer-by-layer convolution feature extraction on the input four-dimensional tensor data, and obtaining the heart beat classification information corresponding to the lead heart beat analysis data through reasoning operation.

Further preferably, the method further includes: establishing and training the LepuEcgCatNet heart beat classification model.

Further preferably, the establishing and training the LepuEcgCatNet heart beat classification model includes:

Based on deep convolutional neural networks AlexNet, Vgg16, ResNet, Inception and open mature deep learning models constructing an end-to-end multi-labeled LepuEcgCatNet heart beat classification model, which is a deep learning model having multi-layer convolutional neural network for classification and identification of the ECG heart beat; and training the LepuEcgCatNet heart beat classification model to obtain model structure data and parameter data, and storing and encrypting the model structure data and the parameter data.

Further preferably, the training includes:

selecting training samples;

converting the training samples into a preset standard data format for storage; and performing data cutting, combining and converting to the training samples, inputting the training samples into the LepuEcgCatNet heart beat classification model for training, storing trained model structure data and parameter data according to Google Protocol Buffers data protocol, and encrypting the model structure data and the parameter data for protecting by using a symmetric encryption algorithm.

In the automatic identification and classification method of ECG heart beat based on artificial intelligence provided by the embodiments of the present disclosure, the heart beat time sequence data and the lead heart beat data are obtained by processing received original ECG digital signals; the lead heart beat data is cut according to the heart beat time sequence data to generate the lead heart beat analysis data; data combination is performed on the lead heart beat analysis data to obtain the one-dimensional heart beat analysis array; data dimension amplification conversion is performed on the one-dimensional heart beat analysis array to obtain the four-dimensional tensor data; and the four-dimensional tensor data is input into the trained LepuEcgCatNet heart beat classification model to obtain the heart beat classification information. The automatic identification and classification method of ECG heart beat based on artificial intelligence according to the present disclosure overcomes a defect that traditional methods, which only rely on independent analyses of a single lead for summarizing result and doing statistics would easily cause classification errors, and greatly enhances the accuracy of the heart beat classification.

DETAILED DESCRIPTION

Technical solutions of the present disclosure will be further described in detail below through accompanying drawings and embodiments.

Figure 1:
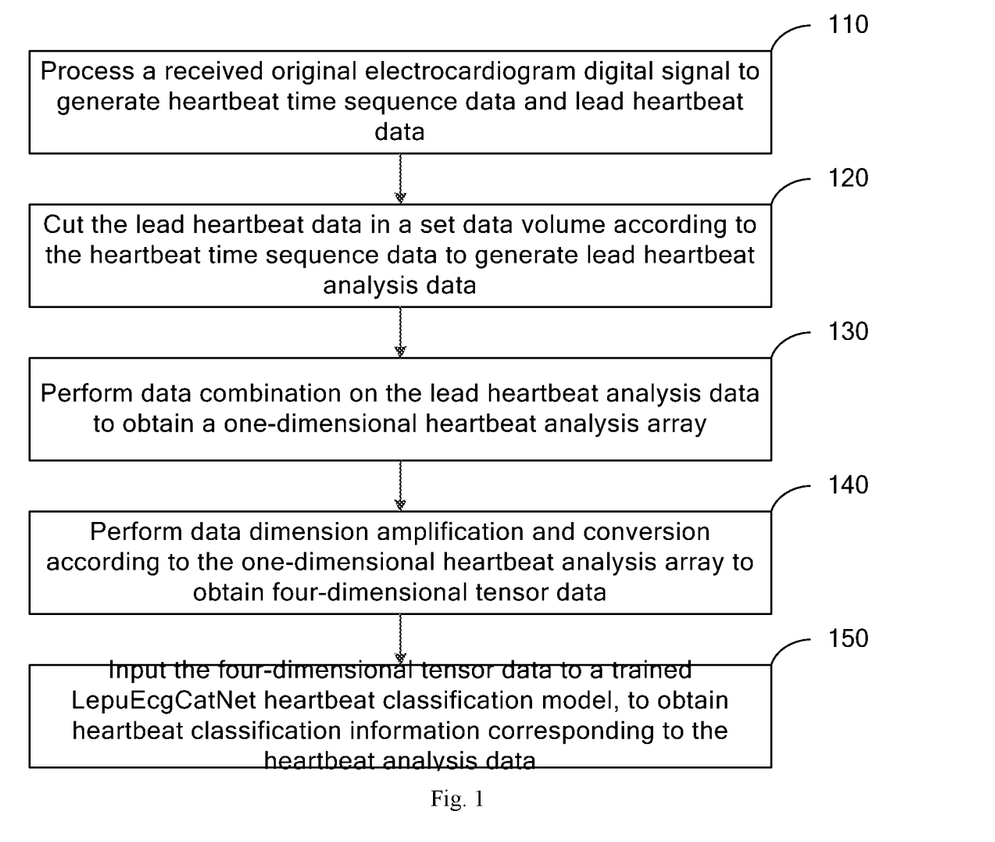
FIG. 1 is a flow chart illustrating an automatic identification and classification method of ECG heart beat based on artificial intelligence self-learning according to an embodiment of the present disclosure.

It is shown in FIG. 1 that a flow chart illustrating an automatic identification and classification method of ECG heart beat based on artificial intelligence self-learning according to an embodiment of the present disclosure, which includes the following steps:

Step 110: received original ECG digital signals are processed to generate heart beat time sequence data and lead heart beat data.

Specifically, ECG electrical analog signals are converted into digital signals by an ECG monitoring device for output, or ECG data obtained through a database or other file means as original data, i.e., original ECG digital signals, is stored by a data storage and transmission apparatus, and which can be transmitted to an analysis system hardware module through WIFI, Bluetooth, USB, 3G/4G/5G mobile communication networks, Internet of Things and other means, and is input into an analysis system execution module as input signals.

Since the generated ECG time sequence data by the original ECG digital signals for recording ECG graphics has great differences in lead labels, data coding formats, gain, precision, data length per second, baseline position and the like due to differences in an acquisition analog circuits, filters and sample rates of ECG devices from different device manufacturers, data pre-processing must be carried out to process uniformly all input ECG time sequence data according to requirements of an analysis flow of the present disclosure. A specific process of data processing and receiving includes the following steps:

1. the original data is resampled according to a preset data sample frequency to obtain time characterization data of each data point under a new sample rate; wherein the time characterization data is used to represent time information of each data point on a time axis of ECG data signals;

2. digital signal filtering is performed on the resampled data to remove high frequency, low-frequency noise and baseline drift;

3. data format converting is performed on the filtered data according to a preset standard data format;

4. heart beat detection processing is performed on the converted data to identify data of multiple heart beats of each lead and form lead heart beat data;

5. interference identification is performed on the lead heart beat data; and 6. the lead heart beat data is combined according to a result of the interference identification and time rules to generate unified heart beat time sequence data.

Step 120: according to the heart beat time sequence data, the lead heart beat data is cut with a set data amount to generate lead heart beat analysis data.

Before cutting the lead heart beat data, a center sample point of the lead heart beat data needs to be determined firstly. A P wave position, an R wave position of a QRS complex, and a T wave position of the lead heart beat data may be selected as the center sample point. The selection of the center sample point of the heart beat data needs to be consistent with that of a center sample point of training samples of a heart beat classification model.

Then, taking the center sample point of the lead heart beat data as a center, according to the time characterization data and the preset data sample frequency, the lead heart beat data is sampled to both sides with the set data amount, so as to obtain the lead heart beat analysis data. The set data amount and the preset data sample frequency should be matched with relevant parameters of input data of a trained LepuEcgCatNet heart beat classification model.

Step 130: data combination is performed on the lead heart beat analysis data to obtain a one-dimensional heart beat analysis array.

Specifically, the lead heart beat analysis data may include single-lead heart beat analysis data and multi-lead heart beat analysis data, and specific processing methods of both are respectively as follows.

The single-lead heart beat analysis data is combined into the one-dimensional heart beat analysis array according to the heart beat time sequence data. Here, a length of the one-dimensional heart beat analysis array is a length of a heart beat time sequence multiplying the set data amount, and contents of which is an arrangement of the heart beat analysis data according to the time sequence.

The data combination is performed on the multi-lead heart beat analysis data to obtain the one-dimensional heart beat analysis array includes the following steps:

a. each piece of time characterization data is acquired according to the heart beat time sequence data;

b. the heart beat analysis data of all leads is acquired according to the time characterization data, and sorted according to lead sequence parameters defined by the classification model;

c. an interference label at a corresponding position of each lead is acquired according to the time characterization data, and sorted according to the lead sequence parameters defined by the classification model;

d. the interference label at the corresponding position of the lead is checked, if it is an interference, replace it with standard interference data with the set data amount, wherein the mentioned-above standard interference data may adopt a full 0 value, a full 1 value, or other preset values;

e. the sorted heart beat analysis data of each lead as sample data is sequentially added to a one-dimensional heart beat analysis array; and f. loop operations a to e until the lead heart beat analysis data corresponding to all of the heart beat time sequence data is converted into sample data and added into the mentioned-above one-dimensional heart beat analysis array, so as to complete a sample data combination of the one-dimensional heart beat analysis array.

Step 140: data dimension amplification conversion is performed on the one-dimensional heart beat analysis array to obtain four-dimensional tensor data.

The LepuEcgCatNet heart beat classification model requires the four-dimensional tensor data (b, h, w, d) as an input data format, wherein b is batch data, h is height data, w is width data, and d is channel data. Specifically, the batch data is a number of input samples, the height data multiply multiplying (x) the width data=a length of each sample, i.e., the set data amount, and the channel data=a number of the leads.

Firstly, an appropriate batch data value is determined according to the set data amount and computer resources used when cutting the lead heart beat data. Specifically, the computer resources refer to a memory size that can be used for deep learning by the computer, including a memory for a graphics card. At the same time, the lepuEcgCatNet heart beat classification model further defines a lead sequence parameter for standard processing of lead sorting when inputting multi-lead sample data.

According to the batch data value and the number of the leads, one-dimensional heart beat analysis array data with a number of the batch data value and a length of the set data amount multiplying (x) the number of the leads is taken out from such one-dimensional heart beat analysis array in turn, and then the data is converted into two-dimensional tensor data, wherein a value of a first dimension is the batch data value, and a value of a second dimension is the set data amount multiplying (x) the number of the leads. In other words, the one-dimensional heart beat analysis array combined in the above step can be converted into a plurality of two-dimensional tensor data with the above size, and each row of the two-dimensional tensor data is one piece of sample data.

Each row of the two-dimensional tensor data further needs to be converted into tensor data with three dimensions, namely height, width and channel. That is, the two-dimensional tensor data needs to be converted into the four-dimensional tensor data.

Specifically, the conversion may be carried out by means of a height fusion, a width fusion or a channel fusion.

Each row of the two-dimensional data tensor may be converted into a three-dimensional data tensor through the height fusion. Specifically, each row of data with the set data amount multiplying (x) the number of the leads is converted into three-dimensional tensor data of which the height is the number of the lead, the width is the set data amount and the channel is 1. In other words, the two-dimensional tensor data is converted into the four-dimensional tensor data (the batch data value, the number of the leads, the set data amount, 1) meeting requirements for input format of the LepuEcgCatNet heart beat classification model.

Each row of the two-dimensional data tensor is converted into a three-dimensional data tensor through the width fusion. Specifically, each row of data with the set data amount multiplying (x) the number of the leads is converted into three-dimensional tensor data , of which the height is 1, the width is the set data amount multiplying (x) the number of the leads and the channel is 1. In other words, the two-dimensional tensor data is converted into the four-dimensional tensor data (the batch data value, 1, the set data amount multiplying (x) the number of the leads, 1) meeting requirements for input format of the LepuEcgCatNet heart beat classification model.

Each row of the two-dimensional data tensor is converted into a three-dimensional data tensor through the channel fusion. Specifically, each row of data with the set data amount multiplying (x) the number of the leads is converted into three-dimensional tensor data of which the height is 1, the width is the set data amount and the channel is the number of the leads. In other words, the two-dimensional tensor data is converted into the four-dimensional tensor data with the first dimension (the batch data value, 1, the set data amount, the number of the leads) meeting requirements for input format of the LepuEcgCatNet heart beat classification model.

Different fusion methods may make the original heart beat analysis data obtain information feature fusion in a time or space scale, which is helpful to improve a classification accuracy of the model.

Step 150: the four-dimensional tensor data is input into the trained LepuEcgCatNet heart beat classification model to obtain heart beat classification information corresponding to the heart beat analysis data.

Specifically, the process for inputting the four-dimensional tensor data into the trained LepuEcgCatNet heart beat classification model for reasoning operation to obtain the heart beat classification information corresponding to the heart beat analysis data includes the following steps:

In the first step, model structure data and parameter data of the trained LepuEcgCatNet heart beat classification model is read according to Google Protocol Buffers data protocol, and the model structure data and the parameter data are protected by a symmetric encryption algorithm, so a decryption operation must be carried out before using.

In the second step, the lead heart beat data received and processed in an operation environment is cut, combined and converted to generate the four-dimensional tensor data meeting requirements for input data format of the LepuEcgCatNet heart beat classification model; and In the third step, the four-dimensional tensor data is input into the read LepuEcgCatNet heart beat classification model, features are extracted through layer-by-layer convolution, and finally, through calculations in turn such as full connection layers, softmax regression classification etc., the heart beat classification information corresponding to the heart beat analysis data is obtained.

The LepuEcgCatNet heart beat classification model can be divided into two types: single-lead heart beat classification model and multi-lead heart beat classification model.

For the heart beat classification of single-lead heart beat data, a LepuEcgCatNet single-lead heart beat classification model is used.

For the heart beat classification of multi-lead heart beat data, generally, a LepuEcgCatNet multi-lead heart beat classification model is used, which is called multi-lead synchronous correlation analysis method. However, in some special cases, the single-lead heart beat classification model can also be used to independently classify part or all of the lead heart beat data of the multi-lead heart beat data, and then a classification voting decision calculation is carried out according to a classification result of each lead and lead weight reference coefficients to obtain a final classification result. This method is called a multi-lead voting decision method. Specifically, the lead weight reference coefficients are voting weight coefficients of each lead for different heart beat classifications obtained by a Bayesian statistical analysis on ECG big data.

Figure 3:
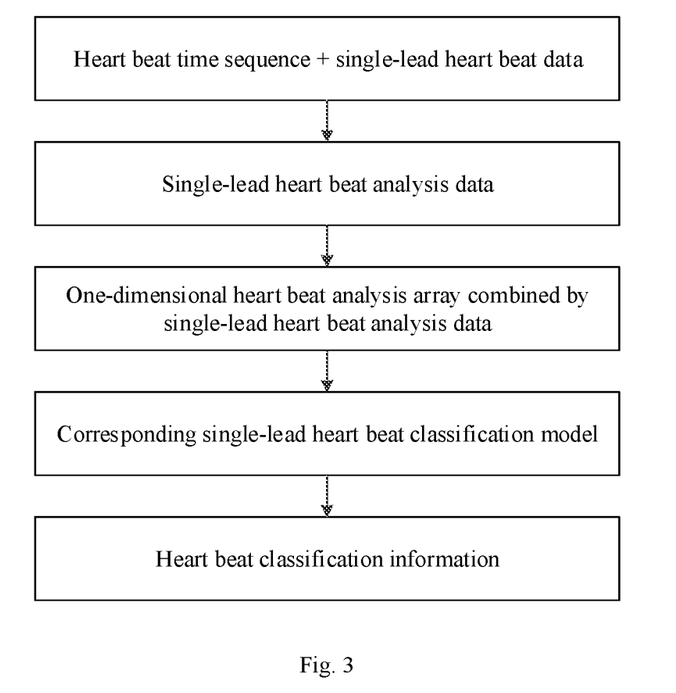
FIG. 3 is a schematic diagram illustrating a process for a single-lead heart beat data classification method according to an embodiment of the present disclosure.

Specifically, FIG. 3 illustrates a process of a single-lead heart beat data classification method:

According to the heart beat time sequence data, the single-lead heart beat analysis data is generated by cutting the single-lead heart beat data with the first data amount, and is input into the trained LepuEcgCatNet single-lead heart beat classification model corresponding to such lead to perform feature extraction and analysis of an amplitude and time characterization data, so as to obtain the classification information of the single-lead heart beat data.

Figure 4:
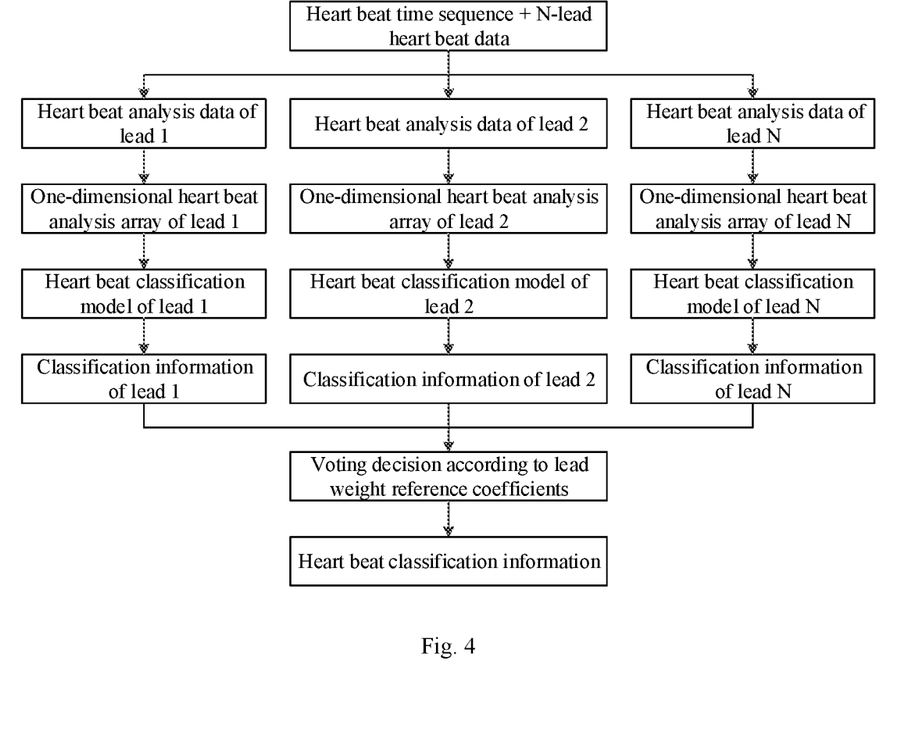
FIG. 4 is a schematic diagram illustrating a process for a multi-lead voting decision classification method according to an embodiment of the present disclosure.

Specifically, FIG. 4 illustrates a process for using the lead voting decision method to classify the multi-lead heart beat data:

in the first step, the heart beat data of each lead is cut with a second data amount according to the heart beat time sequence data to generate the heart beat analysis data of each lead;

in the second step, feature extraction and analysis of an amplitude and time characterization data are performed on the heart beat analysis data of each lead according to the trained LepuEcgCatNet single-lead heart beat classification model corresponding to each lead, so as to obtain the classification information of each lead; and in the third step, the classification voting decision calculation is performed according to the classification information of each lead and the lead weight reference coefficients to obtain primary classification information.

Figure 5:
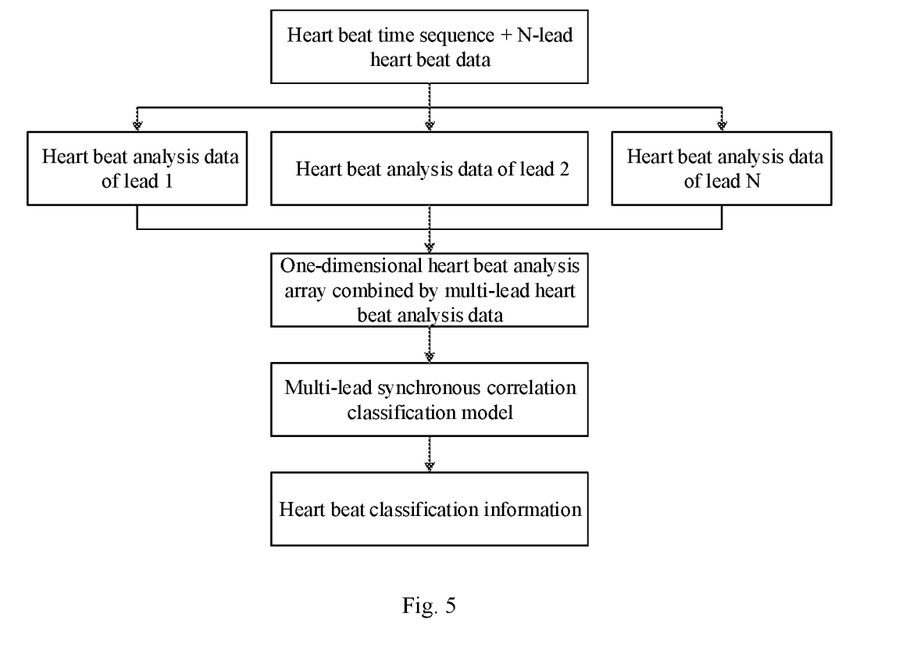
FIG. 5 is a schematic diagram illustrating a process for a lead synchronous correlation classification method according to an embodiment of the present disclosure.

Specifically, FIG. 5 illustrates a process for using a lead synchronous correlation classification method to classify the multi-lead heart beat data:

in the first step, the heart beat data of each lead is cut with a third data amount according to the heart beat time sequence data to generate the heart beat analysis data of each lead; and in the second step, feature extraction and analysis of a synchronous amplitude and time characterization data are performed on the heart beat analysis data of each lead according to the trained LepuEcgCatNet multi-lead heart beat classification model, so as to obtain primary classification information of the heart beat analysis data.

Figure 2:
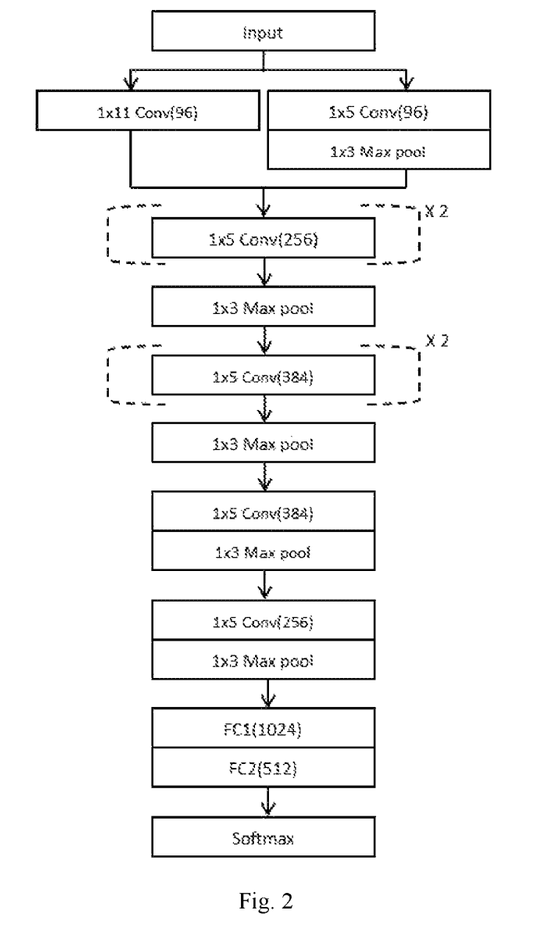
FIG. 2 is a schematic diagram illustrating a LepuEcgCatNet heart beat classification model according to an embodiment of the present disclosure.

The structure of the LepuEcgCatNet heart beat classification model is shown in FIG. 2. The LepuEcgCatNet heart beat classification model is an end-to-end multi-label deep convolutional neural network classification model constructed by inspiring of mature and disclosed models such as AlexNet, VGG16 and Inception, which are based on artificial intelligence deep learning, and more is a deep learning model specifically aiming at ECG analysis requirements and data characteristics. Specifically, the network of the model is a seven-layer convolution network, and each convolution is followed by an activation function. A first layer is a convolution layer having two different scales, followed by six convolution layers. The number of convolution kernels of the seven-layer convolution are 96, 256, 256, 384, 384, 384 and 256, respectively. Except for the convolution kernel of the first layer, which has two scales of 5 and 11, the convolution kernels of other layers have a scale of 5. Third, fifth, sixth and seventh convolution layers are followed by a pooling layer. Finally, two full connection layers follow. Specifically, a training process of the LepuEcgCatNet heart beat classification model includes the following steps:

In the first step, training data is selected. 17 million data samples of 300,000 patients in a training set are used for training. These samples are generated by accurately labeling the data according to requirements of ECG analysis and diagnosis. Labeling is mainly for common arrhythmias, conduction block, ST segment and T wave changes, which can meet model training in different application scenes. Specifically, labeled information is stored in a preset standard data format. In the preprocessing of the training data, in order to increase a generalization ability of the model, small sliding is made for a classification with a small sample size to expand the data. Specifically, the data is moved 2 times based on each heart beat, t according to a certain step (such as 10-50 data points), so that the data can be increased by 2 times, and an identification accuracy of classification samples with the small amount of data is improved. The generalization ability has also been verified to be improved from the actual results.

In the second step, the training samples are converted into a preset standard data format for storage.

In the third step, the training samples are performed data cutting, combining and converting, and the converted data meets requirements of the LepuEcgCatNet heart beat classification model for the input data format, and which can be used for the training of the model.

In the fourth step, in an actual training process, two GPU servers are used for dozens of round-robin training. After the training converges, independent test data with a certain data amount is used to test models trained with different iteration times, and a model with the highest test accuracy is selected as the LepuEcgCatNet heart beat classification model. The model and the parameter data are stored according to Google Protocol Buffers data protocol and protected by the symmetric encryption algorithm.

An interception length of the training data can be from 1 second to 10 seconds. For example, for a segment D[500]

with a sample rate of 200 Hz, a sample length of 2.5 s, a obtained set data amount of 500 ECG voltage values (millivolts), data conversion is performed according to the batch data and a number of the leads N, and final four-dimensional tensor data can be obtained: four-dimensional tensor data Inputdata (the batch data, N, 500, 1) in height fusion mode, four-dimensional tensor data Inputdata (the batch data, 1, 500×N, 1) in width fusion mode or four-dimensional tensor data Inputdata (the batch data, 1, 500, N) in channel fusion mode. All input data is randomly scattered before training, which ensures convergence of the training process. At the same time, collection of too many samples from the ECG data of a same patient is controlled, which improves the generalization ability of the model, that is, an accuracy rate in a real scene.

The automatic identification and classification method of ECG heart beat based on artificial intelligence according to the present disclosure improves a defect that classification errors are easy to be obtained by only relying on independent analyses of a single lead for result summary and statistics in traditional methods, and greatly improves the accuracy of the heart beat classification.

Those skilled in the art should further realize that the units and algorithm steps of the examples described in the embodiments disclosed herein can be implemented in electronic hardware, computer software, or a combination of the two. In order to clearly illustrate the interchangeability of hardware and software, the composition and steps of each example have been generally described according to functions in the above description. Whether these functions are implemented in hardware or software depends on the specific application and design constraints of the technical solutions. Those skilled in the art may use different methods to implement the described functions for each specific application, but such implementation should not be considered to be beyond the scope of the present disclosure.

The steps of methods or algorithm described in the embodiments disclosed herein may be implemented in hardware, a software module executed by a processor, or a combination of the two. The software module may be placed in random access memory (RAM), memory, read only memory (ROM), electrically programmable ROM, electrically erasable programmable ROM, registers, hard disks, removable disks, CD-ROM, or any other form of storage medium known in the technical field.

The specific embodiments described above have further explained the purpose, technical solution and beneficial effects of the present disclosure in detail. It should be understood that the above is only specific embodiments of the present disclosure and is not used to limit the scope of protection of the present disclosure. Any modification, equivalent substitution, improvement, etc. made within the spirit and principles of the present disclosure should be included in the scope of protection of the present disclosure.

What is claimed is:

1. An automatic identification and classification method of ECG heart beat based on artificial intelligence, comprising:
processing received original ECG digital signals to generate heart beat time sequence data and lead heart beat data;
cutting the lead heart beat data with a set data amount to generate lead heart beat analysis data according to the heart beat time sequence data;
performing data combination on the lead heart beat analysis data to obtain a one-dimensional heart beat analysis array;
performing data dimension amplification conversion on the one-dimensional heart beat analysis array to obtain four-dimensional tensor data; and
inputting the four-dimensional tensor data into a trained LepuEcgCatNet heart beat classification model to obtain heart beat classification information corresponding to the lead heart beat analysis data.

2. The automatic identification and classification method of ECG heart beat according to claim 1, wherein the cutting the lead heart beat data with a set data amount to generate lead heart beat analysis data according to the heart beat time sequence data, comprises:
determining a center sample point of the lead heart beat data according to the heart beat time sequence data; and
taking the center sample point as a center, according to time characterization data and a preset data sample frequency, data sampling the lead heart beat data to both sides with the set data amount, so as to obtain the lead heart beat analysis data.

3. The automatic identification and classification method of ECG heart beat according to claim 1, wherein the lead heart beat analysis data is single-lead heart beat analysis data, and the performing data combination on the lead heart beat analysis data to obtain a one-dimensional heart beat analysis array comprises:
combining the single-lead heart beat analysis data into the one-dimensional heart beat analysis array according to the heart beat time sequence data.

4. The automatic identification and classification method of ECG heart beat according to claim 1, wherein the lead heart beat analysis data is multi-lead heart beat analysis data, and the performing data combination on the lead heart beat analysis data to obtain a one-dimensional heart beat analysis array comprises:
combining the multi-lead heart beat analysis data into the one-dimensional heart beat analysis array according to lead parameters and the heart beat time sequence data.

5. The automatic identification and classification method of ECG heart beat according to claim 1, wherein the performing data dimension amplification conversion on the one-dimensional heart beat analysis array to obtain four-dimensional tensor data comprises:
converting the one-dimensional heart beat analysis array into a four-dimensional tensor data input format required by the trained LepuEcgCatNet heart beat classification model in a specific conversion mode; wherein the four-dimensional tensor data has four factors, which are height data, width data, channel data and batch data;
wherein the specific conversion mode comprises:
determining the height data and the width data according to a length of input samples, and generating fusion data according to the height data, the width data or the channel data; wherein the channel data is a number of leads; and
generating the four-dimensional tensor data according to the batch data and the fusion data; wherein the batch data is a number of the input samples.

6. The automatic identification and classification method of ECG heart beat according to claim 1, wherein the inputting the four-dimensional tensor data into a trained LepuEcgCatNet heart beat classification model to obtain heart beat classification information corresponding to the lead heart beat analysis data comprises:
according to the trained LepuEcgCatNet heart beat classification model, performing layer-by-layer convolution feature extraction on the input four-dimensional tensor data, and obtaining the heart beat classification information corresponding to the lead heart beat analysis data through reasoning operation.

7. The automatic identification and classification method of ECG heart beat according to claim 6, the method further comprises: establishing and training the trained LepuEcgCatNet heart beat classification model.

8. The automatic identification and classification method of ECG heart beat according to claim 7, the establishing and training the trained LepuEcgCatNet heart beat classification model comprises:
   based on deep convolutional neural networks AlexNet, Vgg16, ResNet, Inception and open mature deep learning models, constructing an end-to-end multi-labeled LepuEcgCatNet heart beat classification model which is a deep learning model having multi-layer convolutional neural network for the automatic identification and classification method of the ECG heart beat; and
   training the end-to-end multi-labeled LepuEcgCatNet heart beat classification model to obtain model structure data and parameter data, and storing and encrypting the model structure data and the parameter data.

9. The method according to claim 7, the training comprises:
   selecting training samples;
   converting the training samples into a preset standard data format for storage; and
   performing data cutting, combining and converting to the training samples, inputting the training samples into the trained LepuEcgCatNet heart beat classification model for training, storing trained model structure data and parameter data according to Google Protocol Buffers data protocol, and encrypting the trained model structure data and the parameter data for protecting by using a symmetric encryption algorithm.

10. The automatic identification and classification method of ECG heart beat according to claim 2, wherein the lead heart beat analysis data is single-lead heart beat analysis data, and the performing data combination on the lead heart beat analysis data to obtain a one-dimensional heart beat analysis array comprises:
    combining the single-lead heart beat analysis data into the one-dimensional heart beat analysis array according to the heart beat time sequence data.

11. The automatic identification and classification method of ECG heart beat according to claim 10, wherein the lead heart beat analysis data is multi-lead heart beat analysis data, and the performing data combination on the lead heart beat analysis data to obtain a one-dimensional heart beat analysis array comprises:
    combining the multi-lead heart beat analysis data into the one-dimensional heart beat analysis array according to lead parameters and the heart beat time sequence data.

12. The automatic identification and classification method of ECG heart beat according to claim 11, wherein the performing data dimension amplification conversion on the one-dimensional heart beat analysis array to obtain four-dimensional tensor data comprises:
    converting the one-dimensional heart beat analysis array into a four-dimensional tensor data input format required by the trained LepuEcgCatNet heart beat classification model in a specific conversion mode; wherein the four-dimensional tensor data has four factors, which are height data, width data, channel data and batch data;
    wherein the specific conversion mode comprises:
        determining the height data and the width data according to a length of input samples, and generating fusion data according to the height data, the width data or the channel data; wherein the channel data is a number of leads; and
        generating the four-dimensional tensor data according to the batch data and the fusion data; wherein the batch data is a number of the input samples.

13. The automatic identification and classification method of ECG heart beat according to claim 12, wherein the inputting the four-dimensional tensor data into a trained LepuEcgCatNet heart beat classification model to obtain heart beat classification information corresponding to the lead heart beat analysis data comprises:
    according to the trained LepuEcgCatNet heart beat classification model, performing layer-by-layer convolution feature extraction on the input four-dimensional tensor data, and obtaining the heart beat classification information corresponding to the lead heart beat analysis data through reasoning operation.

14. The automatic identification and classification method of ECG heart beat according to claim 13, the method further comprises: establishing and training the trained LepuEcgCatNet heart beat classification model.

15. The automatic identification and classification method of ECG heart beat according to claim 14, the establishing and training the LepuEcgCatNet heart beat classification model comprises:
    based on deep convolutional neural networks AlexNet, Vgg16, ResNet, Inception and open mature deep learning models, constructing an end-to-end multi-labeled LepuEcgCatNet heart beat classification model which is a deep learning model having multi-layer convolutional neural network for the automatic identification and classification method of the ECG heart beat; and
    training the end-to-end multi-labeled LepuEcgCatNet heart beat classification model to obtain model structure data and parameter data, and storing and encrypting the model structure data and the parameter data.

16. The method according to claim 14, the training comprises:
    selecting training samples;
    converting the training samples into a preset standard data format for storage; and
    performing data cutting, combining and converting to the training samples, inputting the training samples into the end-to-end multi-labeled LepuEcgCatNet heart beat classification model for training, storing trained model structure data and parameter data according to Google Protocol Buffers data protocol, and encrypting the trained model structure data and the parameter data for protecting by using a symmetric encryption algorithm.

* * * * *